United States Patent
Endo

(10) Patent No.: US 7,127,031 B2
(45) Date of Patent: Oct. 24, 2006

(54) RADIATION IMAGING APPARATUS, RADIATION IMAGING SYSTEM AND RADIATION IMAGING METHOD

(75) Inventor: Tadao Endo, Saitama (JP)

(73) Assignee: Canon Kabushiki Kaisha, Tokyo (JP)

( * ) Notice: Subject to any disclaimer, the term of this patent is extended or adjusted under 35 U.S.C. 154(b) by 81 days.

(21) Appl. No.: 10/827,435

(22) Filed: Apr. 20, 2004

(65) Prior Publication Data

US 2004/0213377 A1 Oct. 28, 2004

(51) Int. Cl.
*H05G 1/64* (2006.01)
*H05G 1/32* (2006.01)

(52) U.S. Cl. ............................ 378/98.11; 378/89.12; 378/111

(58) Field of Classification Search .... 378/98.8–98.12, 378/101, 111, 114
See application file for complete search history.

(56) References Cited

U.S. PATENT DOCUMENTS

| | | | |
|---|---|---|---|
| 6,683,934 B1 * | 1/2004 | Zhao et al. | 378/9 |
| 2003/0169848 A1 * | 9/2003 | Jabri et al. | 378/98.9 |

FOREIGN PATENT DOCUMENTS

| | | |
|---|---|---|
| JP | 2-273873 | 11/1990 |
| JP | 3-106343 | 5/1991 |
| JP | 3-133276 | 6/1991 |
| JP | 5-260382 | 10/1993 |

* cited by examiner

*Primary Examiner*—Edward J. Glick
*Assistant Examiner*—Irakli Kiknadze
(74) *Attorney, Agent, or Firm*—Fitzpatrick, Cella, Harper & Scinto

(57) ABSTRACT

A radiation detector includes radiation detection elements for detecting radiations which have penetrated an object as electric signals, with the elements arranged in a two-dimensional array, and an image display controller for producing a radiation image of the object detected as the electric signals with the radiation detector as continuous images including a plurality of frames. The image display controller switches a tube voltage of a radiation source for emitting the radiations between a first voltage at a time of producing odd images and a second voltage at a time of producing even images and controls a display device to continuously display a plurality of processed images as a dynamic image. Each of the processed images are obtained by performing a subtraction process between an odd image of the odd images and an even image of the even images, wherein the even image is derived in succession to the odd image.

12 Claims, 6 Drawing Sheets

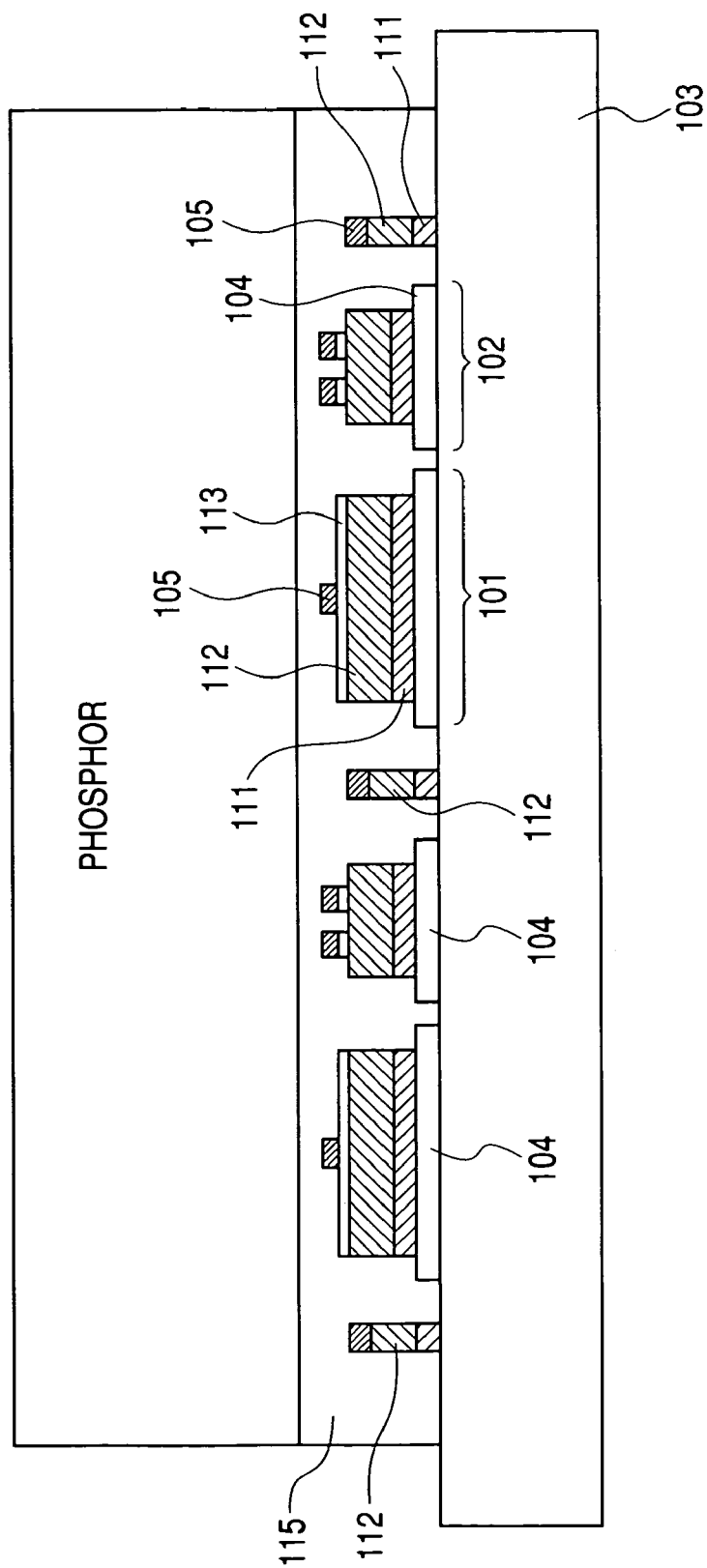

REFRESH MODE

PHOTOELECCTRIC
CONVERSION MODE

SATURATED STATE

RADIATION IMAGING APPARATUS, RADIATION IMAGING SYSTEM AND RADIATION IMAGING METHOD

BACKGROUND OF THE INVENTION

1. Field of the Invention

The present invention relates to a radiation imaging apparatus suitable to be used for a medical diagnosis, an industrial non-destructive inspection, and more particularly to a radiation imaging apparatus and a radiation imaging system suitable for radiography for obtaining a dynamic image. Hereupon, the radiation is not limited to X-rays, but includes α-rays, β-rays, γ-rays and the like.

2. Description of Related Art

Conventional X-ray imaging systems include a film radiographing system and a digital radiographing system. The film radiographing system irradiates a patient with X-rays to expose a film with the X-rays which have penetrated the patient. The digital radiographing system converts the X-rays which have penetrated the patient into electric signals, and detects the electric signals as digital values with an AD converter to take the digital values into a memory. The present main current of the latter system is a system for performing digitalization by accumulating X-ray images in photostimulable phosphor called as an imaging plate (hereinafter referred to as an "IP"), the representative material of which is BaFBr:Eu, and after that by scanning the IP with laser beams to obtain visible rays from the IP. The system, then, converts the obtained visible rays from the IP into electric signals with a photomultiplier tube or the like to digitize the electric signals.

Another digitalization system has lately been put to practical use. In the digitalization system, X-rays irradiate X-ray visible conversion phosphor using $Gd_2O_2S$:Tb or CsI:Tl as the representative material thereof, and visible rays are emitted in proportion to the dosage of the X-rays. The emitted visible rays are converted into electric signals by an amorphous silicon photosensor to be digitized. An element for implementing the digitization system is called as a flat panel detector (hereinafter referred to as a "FPD"). A type of the FPD does not use the X-ray visible conversion phosphor, but uses Se or $PbI_2$ as a material to absorb X-rays directly and to convert the absorbed X-rays into electric signals.

In addition, there is a further apparatus. The apparatus irradiates a primary phosphor with X-rays, and accelerates and focuses photoelectrons emitted from the fluorescent screen of the primary phosphor with an electron lens onto a secondary fluorescent scree. Then, the apparatus converts a fluorescent image (an X-ray image) on the secondary fluorescent screen into electric signals with an image pickup tube or charge coupled elements (CCD's). The apparatus is called an image intensifier (I.I.), and is generally used for fluorography. Also by this apparatus, electric signals can be detected as digital values, and the system adopted by this apparatus is one of the digital radiographing systems.

As described above, a variety of apparatus for digitalizing X-ray images exist. The demands for digitalization at medical scenes have recently been increasing more and more. The digitalization of image data could bring about the advantage of the easiness of the recording, the displaying, the printing and the holding of radiographed data. Moreover, the image processing of radiographed data using a computer enables a doctor to be aided at the time of a diagnosis by the interpretation of a radiogram. Moreover, it is said that an automatic diagnosis only by a computer without any doctors for the interpretation of a radiogram will be able to be realized in the near future.

Even at current medical scenes in which the radiation imaging apparatus are shifting from the film radiographing system, the so-called analogy radiographing system, to the aforesaid digital radiographing system, simple X-ray radiography is performed as a first step of X-ray photography. For example, in case of a chest region, the X-ray radiography is called as chest simple X-ray radiography. The chest simple X-ray radiography performs the X-ray radiography of the front face (or the side face) of the chest region of a human body. It is said that a radiographing area of the so-called half size (35 cm×43 cm) or more, possibly the size of 43 cm×43 cm or more, is generally necessary for covering the whole area of the chest region (the upper half) of a human body. For the chest simple X-ray radiography, the digital radiographing system using the FPD is more expected in the future than the one using the I.I., which is considered to have a problem of distortion at peripheral parts of an image.

The chest simple X-ray radiography can expose the information of a body in the vicinity of the lung field of the upper half of the body, such as the information of an esophagus, a trachea, pulmonary blood vessels, alveoli, a heart, heart blood vessels, a diaphragm, costae and clavicles, by X-ray radiography for a radiograph at one time. Accordingly, the chest simple X-ray radiography is frequently performed as the radiography effective for the screening of foci. However, penetrated images are observed on the principle thereof in the radiography. Consequently, when a focus exists behind such a tissue as a costa, heart blood vessels, or a diaphragm, the focus doubly overlaps the tissue in a penetrated image. Hence, there are some cases where it is difficult to find (or discover) the shadow of the focus. Thereby, the chest simple X-ray radiography has the problems that the efficiency of the screening of foci decreases, and that the discovery of the foci is retarded.

As means for solving the problems, a method has been realized. In the method, two imaging plates (IP's) are used for radiography at two times under different tube voltages, and the shadow of a bone part is removed by performing a subtraction process between X-ray images obtained from the two IP's. The method is called as an energy subtraction process (ES process). The method is the radiography using the phenomenon such that, when the energy of X-rays is changed, the absorption degrees of the energy by bone tissues are different from those by soft tissues such as blood vessels, lymphatic vessels and nerves.

As an example of the ES process, Japanese Patent Application Laid-Open No. H2-273873 discloses the radiography, in which the subtraction of images radiographed with radiation rays irradiated from a plurality of radiation sources having different radiation energy from one another is performed after the distortion of the images has been corrected on the image signals of the images. Moreover, Japanese Patent Application Laid-Open No. H3-106343 discloses the configuration in which a dual energy generation mechanism is formed on the X-ray irradiation port of an X-ray tube to generate X-rays having different energy from one another at the timing of image collection. Moreover, Japanese Patent Application Laid-Open No. H3-133276 discloses a method of displaying energy subtraction images by obtaining only the images of affected tissues as difference signals to perform display with the images of the affected tissues being added as the depth information at the third dimension. Moreover, Japanese Patent Application Laid-Open No.

H5-260382 discloses a configuration for performing a subtraction by recording images radiographed with X-rays having different energy at different parts on a fluorescent sheet.

However, although the ES process is effective in the point of view of the removal of bone shadows, but the bone shadows are not always removed completely. The ES process particularly has the problem that the bone shadows remain to some figures and physiques of patients and to some kinds of foci. Moreover, foci do not always exist, for example, behind costae. When a focus exists behind a diaphragm or a heart, there is the remaining problem that the ES process for the removal of bone shadows is insufficient to some patient's conditions (physiques, foci) when the ES process is used as the only removal method. Moreover, there is room for further examination of suitable combination methods of the subtraction process and dynamic image display.

SUMMARY OF THE INVENTION

The present invention was made in view of the above-mentioned problems. It is an object of the present invention to provide a radiation imaging apparatus capable of improving the detection rate of abnormal parts of a substrate by enabling the emphasized display of the abnormal parts at the time of radiographing the substrate to obtain an image of the radiations which penetrated the substrate.

A radiation imaging apparatus according to the present invention, includes: radiation detection means including radiation detection elements for detecting radiations which have penetrated an object as electric signals, the elements arranged in a two-dimensional array; and image display control means for producing a radiation image of the object detected as the electric signals with the radiation detection means as continuous images including a plurality of frames, the image display control means switching a tube voltage of a radiation source for emitting the radiations between a voltage at a time of producing a (2m−1)th odd image and another voltage at a time of producing a 2mth even image, where m is a natural number, the image display control means further controlling a display device to display a processed image as a dynamic image, the processed image being obtained by performing a subtraction process between the (2m−1)th odd image and the 2mth even image.

According to the present invention, radiography is performed while alternatively irradiating radiations having energy different from each other at the time of producing the (2m−1)th odd image and at the time of producing the 2mth even image, and the subtraction process between the odd image and the even image is performed to display the processed image obtained by the subtraction process on the display device. Consequently, the display of the parts where the degrees of changes are larger can be enhanced to be blacker or whiter against that of the parts where the degrees of changes are not so large.

Thereby, for example, a doctor can recognize the parts where the degrees of changes are larger while performing the interpretation of a radiograph when the doctor performs a diagnosis. Consequently, the detection rate of abnormal parts such as foci can be improved.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 5 is a sectional view taken along a line 5—5 of the photoelectric conversion circuit unit shown in FIG. 4.

DETAILED DESCRIPTION OF THE PREFERRED EMBODIMENTS

In the following, the attached drawings will be referred to while the preferred embodiment of the radiation imaging apparatus of the present invention is described. Incidentally, in the embodiment of the present invention, X-rays will be exemplified as radiations to be described.

First Embodiment

Figure 1:
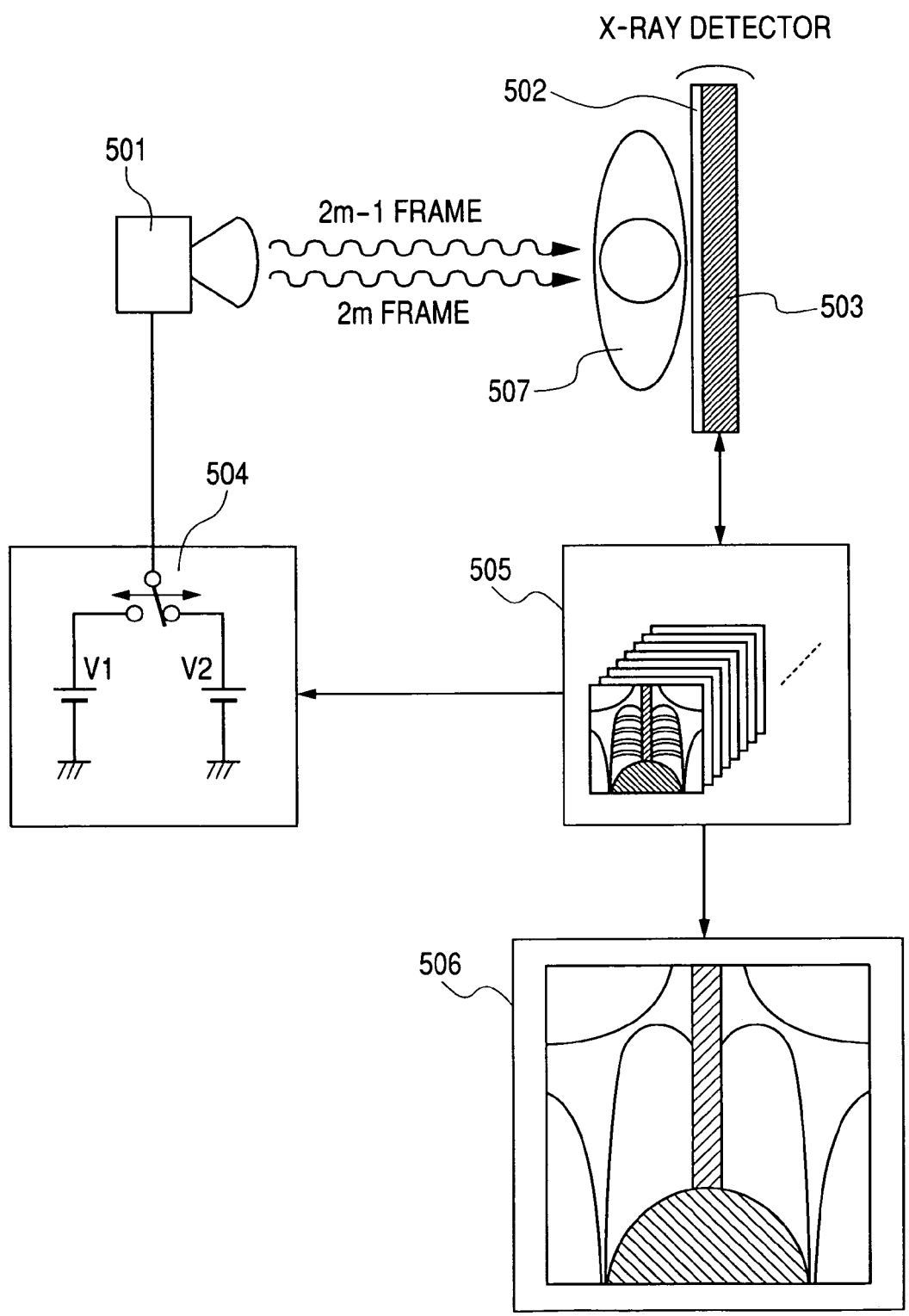
FIG. 1 is a schematic view showing an X-ray imaging system of an embodiment of the present invention.

FIG. 1 is a schematic view of an X-ray imaging system of the embodiment of the present invention.

X-rays emitted from an X-ray tube 501 irradiates an object 507. The object 507 is mainly a patient. The X-rays which have penetrated the patient is converted to visible light by an X-ray visible conversion phosphor 502. The visible light from the phosphor 502 is converted to electric signals by a photoelectric conversion device 503. Consequently, the X-ray penetration image of the subject 507 (patient) is converted into the electric signals. The X-ray visible conversion phosphor 502 and the photoelectric conversion device 503 are configured to adhere to each other substantially by being bonded with each other, and both of them are integrally called as an X-ray detector. An X-ray power source 504 supplies a high voltage for accelerating electrons in the X-ray tube 501, and the X-ray power source 504 is called as an X-ray generation device together with the X-ray tube 501.

An image processor 505 is the so-called computer provided with the function of recording X-ray image information, which is converted into electric signals, the function of operating obtained image data, the function of generating control signals for operating the X-ray detector, the function of controlling the X-ray generation device, and the function of making a cathode ray tube (CRT) display 506 display images.

The X-ray imaging system of the present embodiment configured to include the X-ray generation device composed of the X-ray power source 504 and the X-ray tube 501; the X-ray imaging apparatus composed of the X-ray detector composed of the X-ray visible conversion phosphor 502 and the photoelectric conversion device 503, and image processor 505; and the CRT display 506 as a display device.

The X-ray imaging apparatus of the present embodiment makes the X-ray tube 501 generate X-rays in pulses, and obtains a plurality of sheets of image information of the patient continuously in time with the X-ray detector. After that, the X-ray imaging apparatus displays radiographed data on the CRT display 506 as a dynamic image with the image processor 505. The feature of the present invention is that the tube voltage of the X-ray tube 501 for obtaining an image F(2m−1) of an odd frame (2m−1) and the tube voltage of the X-ray tube 501 for obtaining an image F(2m) of an even frame (2m), where m indicates a natural number (that is similarly supposed in the following), are set to be different from each other. That is, odd frame images and even frame images are radiographed by the irradiation of pulsed X-rays with the tube voltages being alternatively switched. The image processor 505 performs the subtraction processes (energy subtraction processes) between the odd frame images and the even frame images while displaying dynamic images. Incidentally, the subtraction processes are not always simple subtractions. In the following, the processes will be concretely described.

The image density of a costa component obtained by the radiography of an odd frame with a tube voltage V1 is denoted by D1(V1), and the blood vessel density is denoted by D2(V1). Similarly, the image density of the costa component obtained by the radiography of an even frame with a tube voltage V2 is denoted by D1(V2), and the blood vessel density is denoted by D2(V2). In case of a costa density ratio D1(V2)/D1(V1)=1, costa shadows can be removed by performing the simple subtraction process F(2m)−F(2m−1) in the subtraction process.

However, bone components (though the following is not limited to the bone components) absorb different amounts of X-rays when the energy of the X-rays is changed. Consequently, a difference is produced between the image densities D1(V1) and D1(V2). That is, the costa density ratio D1(V2)/D1(V1) is not one. Accordingly, when the costa density ratio D1(V2)/D1(V1) is set as D1(V2)/D1(V1)=k1, the costa shadows can be removed by performing a subtraction process F(2m)−{k1×F(2m−1)} in the subtraction process.

On the other hand, because blood vessels have tissues (compositions) different from those of the costae, the density ratio of a blood vessel D2(V2)/D2(V1) becomes k2≠K1. Consequently, even if the subtraction process F(2m)−{k1× F(2m−1)} is performed, the image of the blood vessel does not disappear to be displayed. Incidentally, the subtraction process mentioned above is one of subtracting F(2m−1) from F(2m) (k=1). For example, in case of k1=1.5, an image of a treble of F(2m−1) may be subtracted from an image of a double of F(2m). That is, even if the subtraction process is performed between an image of operated F(2m) and an image of operated F(2m−1), the same result can be obtained.

The chest simple X-ray radiography can expose a plurality of tissues, such as an esophagus, a trachea, pulmonary blood vessels, alveoli, a heart, heart blood vessels, a diaphragm, costae and clavicles, by X-ray radiography for a radiograph at one time. The subtraction process may be performed not for removing a certain shadow, but for decreasing the shadows of a plurality of tissues. At that time, as the subtraction process, there is a case where the image of operated F(2m−1) is subtracted from the image of operated F(2m). Moreover, although the example of the removal of the shadow of a costa has been described in the above example, a subtraction process for removing the shadow of a blood vessel may be preformed, and a subtraction operation is selected according to the tissue and the focus, both being wanted to be observed.

In the present invention, when the subtraction process is expressed as F(2m)−F(2m−1), images are continuously displayed on the CRT display 506 in such a manner as "F(2)−F(1)"→"F(4)−F(3)"→"F(6)−F(5)"→ . . . "F(2m)−F (2m−1)" . . . . A doctor can observe the images as a dynamic image while performing a diagnosis.

Energy subtraction images have the merit of the removal or the decrease of the shadows of bone portions such as costae and clavicles in case of, for example, chest X-ray radiography. Moreover, by observing the movements of a patient (such as the movements of the diaphragm and the lung field portion owing to breathing, and the movements of the heart) as a dynamic image, there is the case where foci lurking in the shadows of (behind) costae, clavicles, the diaphragm, the heart and the like are revealed at the processes of the movements. Consequently, the detection ratio of the foci becomes higher. The energy subtraction images are useful not only in case of the chest X-ray radiography, but also in the detection of, for example, the abnormalities of joints composed of bones and tendons (muscles).

In addition, the X-ray radiographing element of the present invention obtains not only a sheet (a time) of a still image, but also a plurality of images, and enables a doctor to observe the movements as the dynamic images of the obtained images. Consequently, the possibility of detecting foci which are difficult to be found from still images in the movements of the body of the patient becomes higher. On the other hand, there is also the case where even the shadow of a normal tissue which is to be detected as a focus in the shadows of a still image can be judged as a normal tissue by the observation of the movements of the tissue with the X-ray apparatus of the present invention, and the precision of a diagnosis is improved.

Because the present invention performs the subtraction process between odd frames and even frames while displaying in case of the radiographing frame rate of fr1 (sheets/second), the frame rate of display is fr1/2 (sheets/second).

Figure 2:
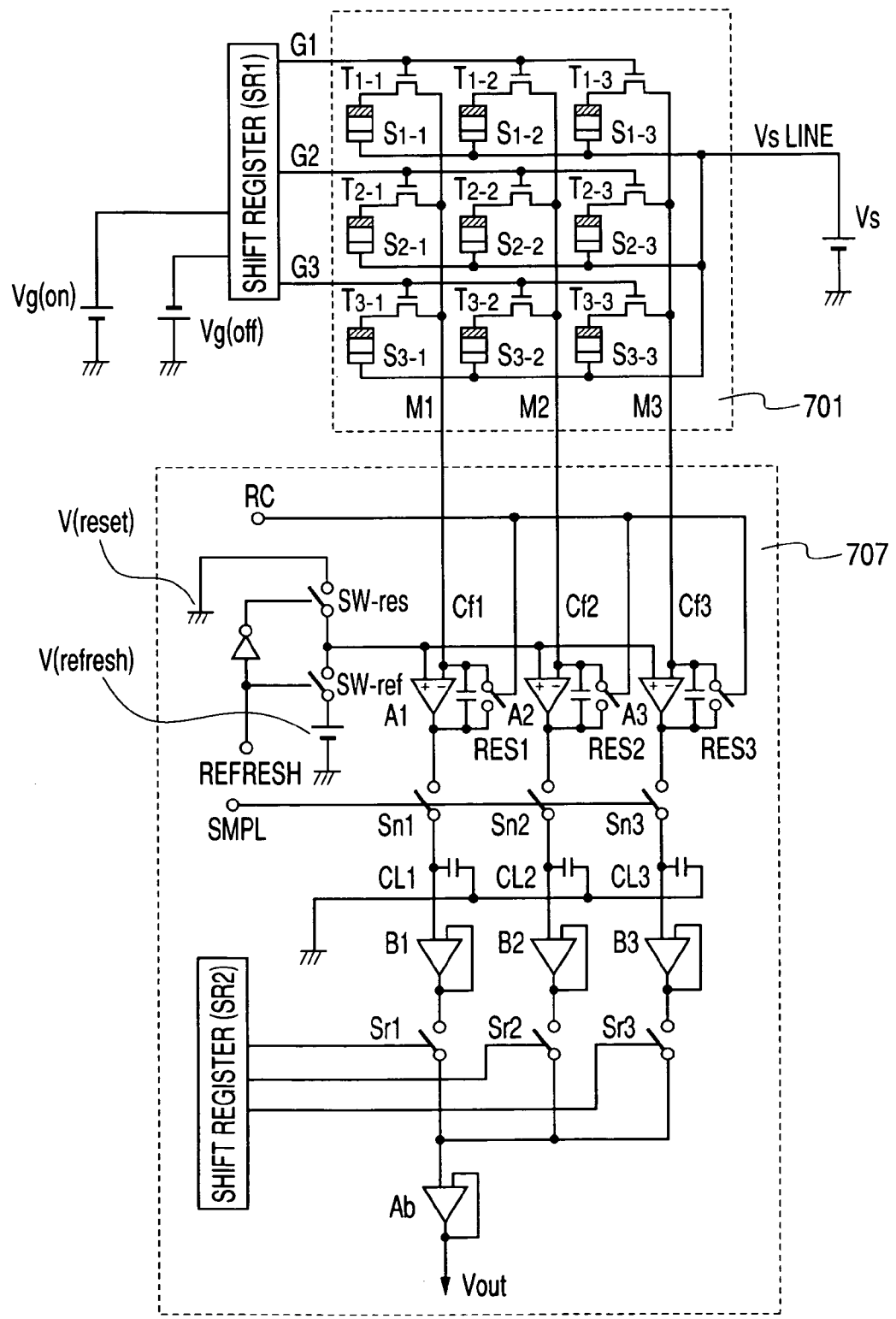
FIG. 2 is a two-dimensional circuit diagram showing a photoelectric conversion device of an X-ray imaging apparatus of an embodiment of the present invention.

FIG. 2 is a two-dimensional circuit diagram showing the photoelectric conversion device 503 of the X-ray imaging apparatus of the embodiment of the present invention. For simplifying the descriptions, FIG. 2 shows a photoelectric conversion circuit unit 701 to have pixels of 3×3 =9.

Hereupon, S1-1 to S3-3 denote metal insulator semiconductor (MIS) type photoelectric conversion elements; T1-1 to T3-3 denote switching elements (thin-film transistors (TFT's)); G1 to G3 denote gate driving wiring for turning on or off the TFT's T1-1 to T3-3; M1 to M3 denote matrix signal wiring; and a Vs line denotes bias wiring for supplying an accumulation bias to the photoelectric conversion elements S1-1 to S3-3.

The photoelectric conversion elements S1-1 to S3-3 each include a gate (G) electrode, which is one on the side painted out into black, and a drain (D) electrode on the opposite side of the G electrode. The D electrodes are commonly used as parts of the bias wiring (Vs line). From the need of the incidence of light, thin $N^+$ layers are used as the D electrodes. The photoelectric conversion elements S1-1 to S3-3, the TFT's T1-1 to T3-3, the gate driving wiring G1 to G3, the matrix signal wiring M1 to M3 and the bias wiring (Vs line) are collectively called as the photoelectric conversion circuit unit 701.

The bias wiring (Vs line) is biased by a bias power source Vs. SR1 denotes a shift register for supplying pulse voltages for driving to the gate driving wiring G1 to G3. To the driving circuit unit (the shift register SR1), a voltage Vg(on)

for turning on the TFT's T1-1 to T3-3 and a voltage Vg(off) for turning off the TFT's T1-1 to T3-3 are supplied from the outside.

A reading circuit unit 707 reads parallel signal outputs from the photoelectric circuit unit 701, and serially converts the read signal outputs to output the converted signals.

A1 to A3 designates operational amplifier, the inverting terminals (−) of which are connected with the matrix signal wiring M1 to M3, respectively. Capacitive elements Cf1 to Cf3 are connected between the inverting terminals (−) and output terminals of the operational amplifiers A1 to A3, respectively. The capacitive elements Cf1 to Cf3 convert the singles of the photoelectric conversion elements S1-1 to S3-3 to voltage quantities by integrating the currents flowing through the capacitative elements Cf1 to Cf3 when the TFT's T1-1 to T3-3 are turned on, respectively. RES1 to RES3 denote switches for resetting the capacitative elements Cf1 to Cf3 to a reset bias V(reset). The switches RES1 to RES3 are connected to the capacitative elements Cf1 to Cf3 in parallel, respectively. In FIG. 2, the reset bias V(reset) is expressed as 0 V, or the ground potential GND.

CL1 to CL3 denote sample hold capacitors for temporarily storing the signals accumulated in the operational amplifiers A1 to A3 and the capacitative elements Cf1 to Cf3. Sn1 to Sn3 denote switches for performing sample hold. B1 to B3 denote buffer amplifiers. Sr1 to Sr3 denote switches for converting parallel signals into serial signals. SR2 denotes a shift register for supplying pulses for the serial conversions to the switches Sr1 to Sr3. Ab denotes a buffer amplifier for outputting the converted serial signals.

SW-res denotes a switch for resetting the non-inverting terminals of the operational amplifiers A1 to A3 to a reset bias V(reset) (0 V in FIG. 2), and SW-ref denotes a switch for refreshing the non-inverting terminals of the operational amplifiers A1 to A3 to a refresh bias V(refresh). These switches are controlled by a signal "REFRESH". When the signal "REFRESH" is a high level "Hi" the switch SW-ref is turned on. When the signal "REFRESH" is a low level "Lo" the switch SW-res is turned on. That is, the reading circuit unit 707 is configured in order that the switches SW-res and SW-ref may not be turned on at the same time.

Figure 3:
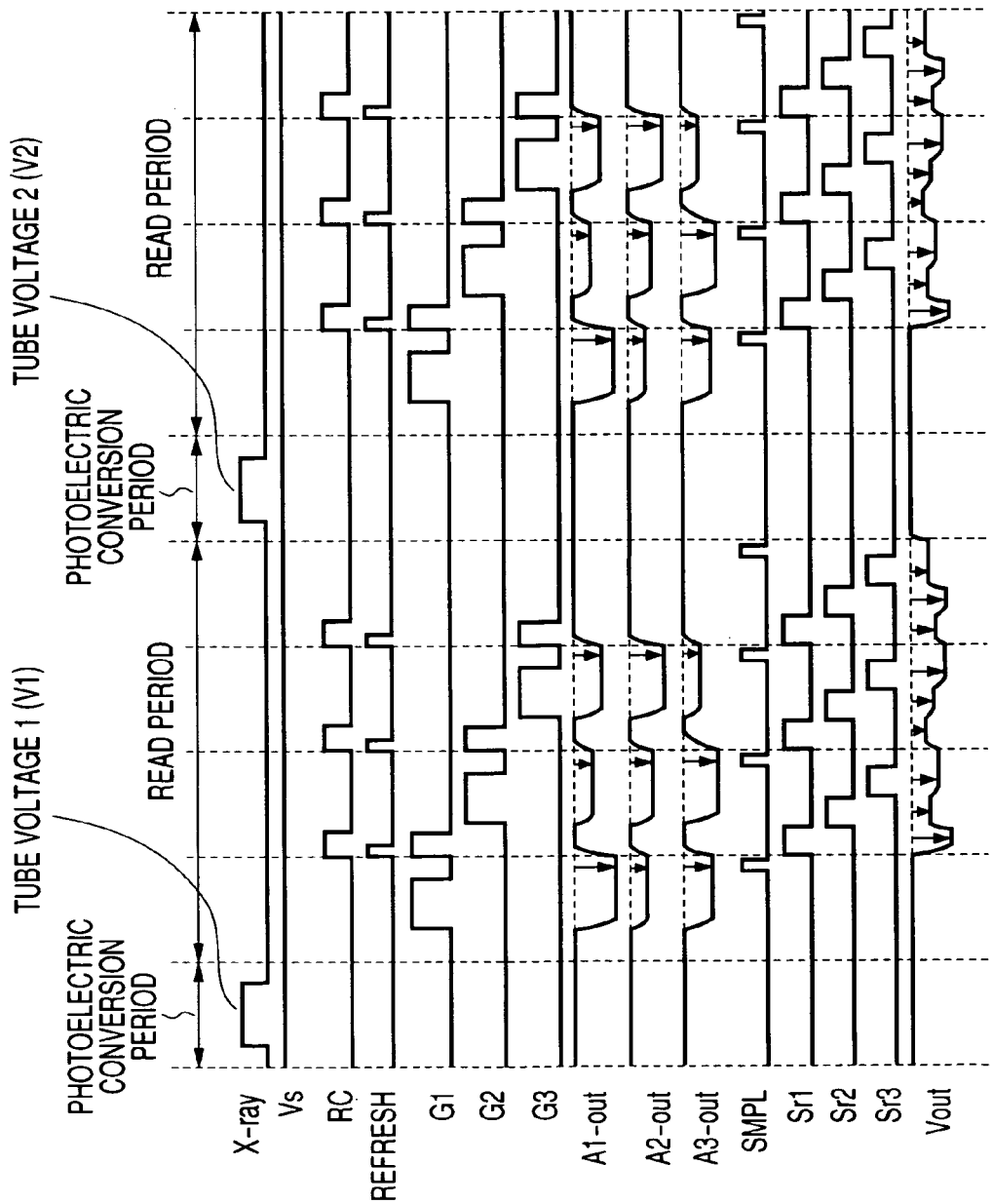
FIG. 3 is a time chart showing the operation of the photoelectric conversion device shown in FIG. 2.

FIG. 3 is a time chart showing the operation of the photoelectric conversion device 503 shown in FIG. 2. FIG. 3 shows the operation of the photoelectric conversion device 503 for two frames. In FIG. 3, the X-ray pulses are shown as if the X-ray pulses have the same amplitudes in a first photoelectric conversion period and a second photoelectric conversion period for the sake of convenience, but the energy of the X-rays is different in the first photoelectric conversion period and in the second photoelectric conversion period in the present invention. In the radiography of a dynamic image, the operation shown in the time chart of FIG. 3 is continuously repeated according to the number of sheets of radiographs. The tube voltages of the X-ray tube 501 are switched in order that the energy of the X-rays corresponding to an odd frame and an even frame may be different from each other.

Next, the operation of the photoelectric conversion device 503 shown in FIG. 2 will be described using the time chart of FIG. 3.

First, a photoelectric conversion period will be described. The D electrodes of all of the photoelectric conversion elements S1-1 to S3-3 is in a biased state by the bias power source Vs (to positive electric potential). All of the signals of the shift register SR1 are at the low level "Lo", and all of the switching TFT's T1-1 to T3-3 are in the off state. When an X-ray source is turned on as a pulse in this state, light irradiates the D electrodes ($N^+$ electrodes) of the respective photoelectric conversion elements S1-1 to S3-3, and carriers of electrons and holes are generated in the i-layers of the photoelectric conversion elements S1-1 to S3-3. Hereupon, the generated electrons move to the D electrodes owing to the bias wiring (Vs line), but the holes are accumulated in interfaces between the i-layers and insulating layers in the photoelectric conversion elements S1-1 to S3-3 to be kept after the turning off of the X-ray.

Successively, a read period will be described. Reading operation is preformed in the order of the photoelectric conversion elements S1-1 to S1-3 at the first row, next the photoelectric conversion elements S2-1 to S2-3 at the second row, and then the photoelectric conversion elements S3-1 to S3-3 at the third row. For reading the photoelectric conversion elements S1-1 to S1-3 at the first row first, the shift register SR1 supplies a gate pulse to the wiring G1 for driving the gates of the TFT's T1-1 to T1-3. At this time, the high level of the gate pulse is the voltage Vg(on) supplied from the outside. Thereby, TFT's T1-1 to T1-3 are turned on, and the signal charges stored in the photoelectric conversion elements S1-1 to Si-3 flows through the TFT's T1-1 to T1-3 as currents. The currents flow into the capacitative elements Cf1 to Cf3 connected to the operational amplifiers A1 to A3, respectively, and the currents are integrated by the capacitative elements Cf1 to Cf3, respectively.

Reading capacitors, though they are not particularly shown in FIG. 2, are added to the matrix signal wiring M1 to M3, and the signal charges are transmitted to the read capacitors on the matrix signal wiring M1 to M3 side through the TFT's T1-1 to T1-3, respectively. However, because the matrix signal wiring M1 to M3 is imaginarily grounded by the reset bias GND of the non-inverting terminals (+) of the operational amplifiers A1 to A3, respectively, no changes of electric potential are caused by the transmission operation, and the electric potential of the matrix signal wiring M1 to M3 is in the state of being held at the ground potential level GND. That is, signal charges are transferred to the capacitative elements Cf1 to Cf3.

The output terminals of the operational amplifiers A1 to A3 change as shown in FIG. 3 according to the signal quantities of the photoelectric conversion elements S1-1 to S1-3, respectively. Hereupon, because the TFT's T1-1 to T1-3 are turned on at the same time, the outputs of the operational amplifiers A1 to A3 simultaneously change. That is, the outputs are parallel outputs. In the state, the tuning on of a signal "SMPL" transfers the output signals of the operational amplifiers A1 to A3 to the sample hold capacitors CL1 to CL3, respectively. Then, the turning off of signal "SMPL" temporarily holds the output signals in the sample hold capacitors CL1 to CL3, respectively.

Successively, the shift register SR2 applies pulses to the switches Sr1, Sr2 and Sr3 in the order. Thereby the signals held by the sample hold capacitors CL1 to CL3 are output from the amplifier Ab in the order of the sample hold capacitors CL1, CL2 and CL3. As a result, the photoelectric conversion signals of the photoelectric conversion elements S1-1, S1-2 and S1-3 for one row are sequentially serially converted to be output.

In the above, the read operation of the photoelectric conversion elements S1-1, S1-2 and S1-3 at the first row has been described. The read operation of the photoelectric conversion elements S2-1 to S2-3 at the second row and the read operation of the photoelectric conversion elements S3-1 to S3-3 at the third row are similarly performed.

The performance of the sample hold of the signals of the operational amplifiers A1 to A3 into the sample hold capacitors CL1 to CL3, respectively, by the signal SMPL for the first row outputs the signals of the photoelectric conversion elements S1-1 to S1-3 from the photoelectric conversion circuit unit 701. Consequently, the refresh operation of the photoelectric conversion elements S1-1 to S1-3 in the photoelectric conversion circuit unit 701 and the reset operation of the capacitative elements Cf1 to Cf3 can be performed while the signals held in the sample hold capacities CL1 to CL3 are serially converted by the switches Sr1 to Sr3 to be output in the read circuit unit 707.

The refresh operation of the photoelectric conversion elements S1-1 to S1-3 is performed by the turning on of the switch SW-ref by the turning of the signal "REFRESH" to the high level "Hi", and by making the switches RES1 to RES3 be in their conductive state with a signal "RC", and further by the application of the voltage Vg(on) to the gate driving wiring G1 of the TFT's T1-1 to T1-3. That is, the refresh operation refreshes the G electrodes of the photoelectric conversion elements S1-1 to S1-3 to the refresh bias V(refresh). After that, the photoelectric conversion elements S1-1 to S1-3 transition to reset operation.

The reset operation is performed by turning the signal "REFRESH" to the low level "Lo" in the state in which the voltage Vg(on) is applied to the gate driving wiring G1 of the TFT's T1-1 to T1-3, and in the state in which the switches RES1 to RES3 are in the conducted state. By the operation, the G electrodes of the photoelectric conversion elements S1-1 to S1-3 is reset to the reset bias V(reset), which is the ground potential level GND, and at the same time the signals accumulated in the capacitative elements Cf1 to Cf3 are reset.

After the completion of the reset operation, next the gate pulse of the gate driving wiring G2 can be applied. That is, during the operation of the serial conversion of the signals of the first row by the shift register SR2, the photoelectric conversion elements S1-1 to S1-3 are refreshed at the same time, and the capacitative elements Cf1 to Cf3 are reset. Then, the signal charges of the second photoelectric elements S2-1 to S2-3 at the second row can be transferred to the matrix signal wiring M1 to M3, respectively, by the shift register SR1.

By the operation described above, the signal charges of all of the photoelectric conversion elements S1-1 to S3-3 from the first row to the third row can be output. Then, the operation of one frame is repeated a plurality of times, and thereby a dynamic image can be obtained.

Figure 4:
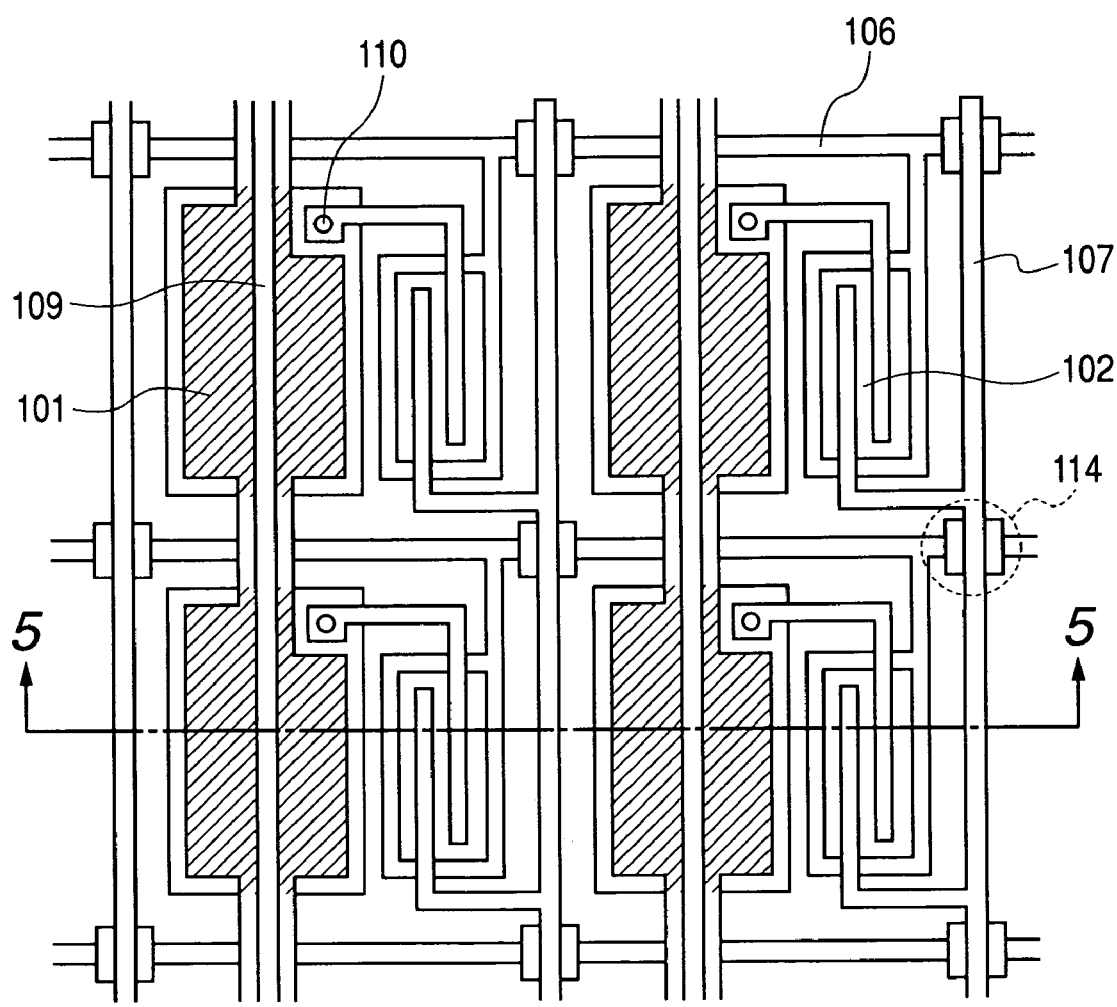
FIG. 4 is a pattern wiring diagram of a photoelectric conversion circuit unit.

FIG. 4 is the pattern wiring diagram of the photoelectric conversion circuit unit 701. FIG. 4 shows MIS type photoelectric conversion elements and switching elements, both made of an amorphous silicon semiconductor thin film as their material. In addition, FIG. 4 also shows wiring for connecting the photoelectric conversion elements and the switching elements. Moreover, FIG. 5 is a sectional view taken along a line 5—5 of the photoelectric conversion circuit unit 701 shown in FIG. 4. In the following descriptions, the MIS type photoelectric conversion elements are simply called as photoelectric conversion elements for simplification.

The photoelectric conversion elements 101 and the switching elements 102 (the amorphous silicon TFT's, which will be simply referred to as TFT's) are formed on the same insulation substrate 103. The lower part electrodes of the photoelectric conversion elements 101 are configures with first metal thin film layers 104, which are the same ones of the lower electors (gate electrodes) of the TFT's 102 to be used commonly. The upper electrodes of the photoelectric conversion elements 101 are configures with second metal thin film layers 105, which are the same ones of the upper electors (source electrodes and drain electrodes) of the TFT's 102 to be used commonly. Moreover, the first and the second metal thin film layers 104 and 105 are commonly used with gate driving wiring 106 and matrix signal wiring 107 in the photoelectric conversion circuit unit 701.

In FIG. 4, four pixel units (2×2) are shown as pixels. Hatched portions in FIG. 4 are light receiving surfaces of the photoelectric conversion elements 101. A reference numeral 109 denotes a power source line for feeding a bias to the photoelectric conversion elements 101. Moreover, a reference numeral 110 denotes a contact hole portion for the connection of each of the photoelectric conversion elements 101 and each of the TFT's 102. The use of the configuration, which is shown in FIG. 4 and uses amorphous silicon semiconductor as its main material, makes it possible to produce the photoelectric conversion elements 101, the switching elements 102, the gate driving wiring 106 and the matrix signal wiring 107 simultaneously on the same substrate (the insulation substrate 103). Consequently, the large sized photoelectric conversion circuit unit 701 can easily and inexpensively be provided.

Next, the device operation of a unit of the photoelectric conversion elements 101 will be described.

Figure 6A:
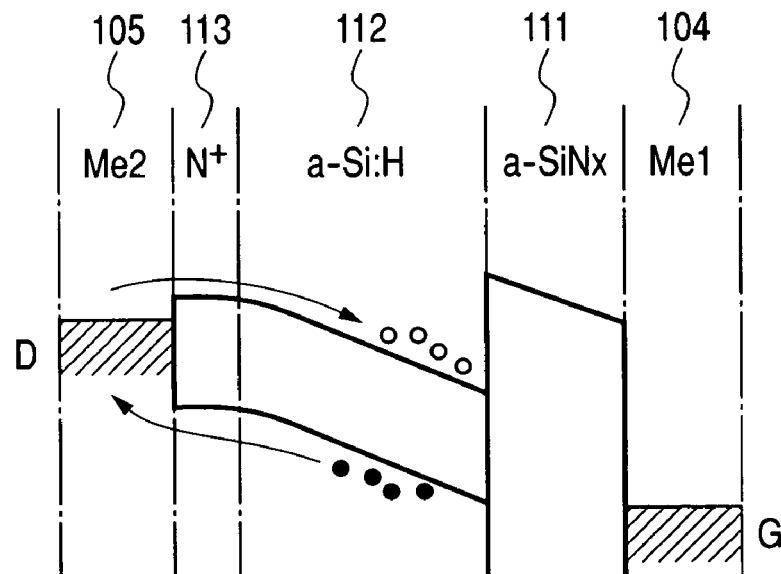
FIGS. 6A, 6B and 6C are energy band diagrams for illustrating the device operation of the photoelectric conversion elements shown in FIGS. 4 and 5.
Figure 6B:
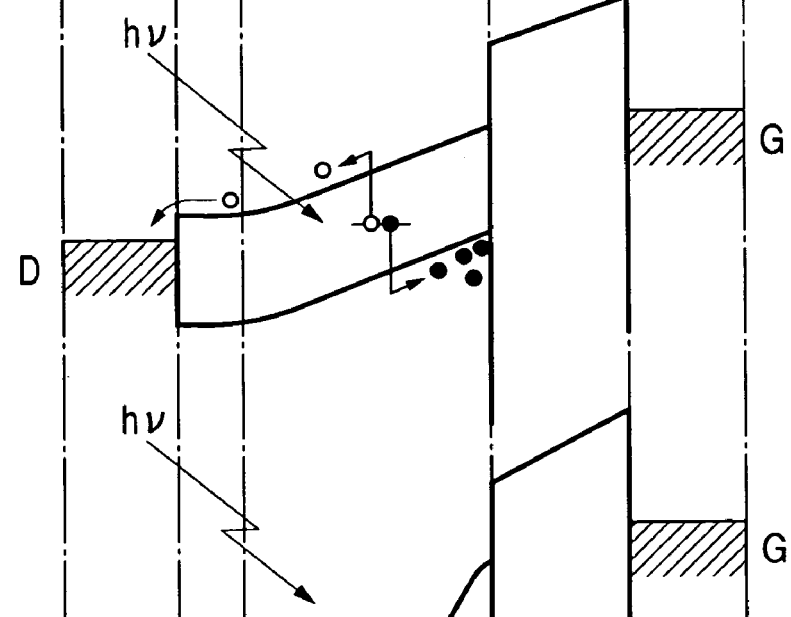
Figure 6C:
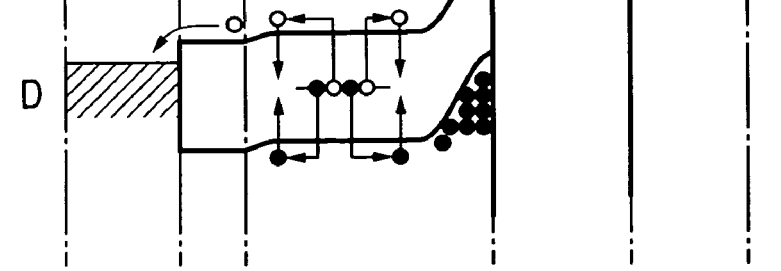

FIGS. 6A, 6B and 6C are energy band diagrams for illustrating the device operation of the photoelectric conversion elements 101 shown in FIGS. 4 and 5. Hereupon, FIG. 6A shows the operation in a refresh mode; FIG. 6B shows the operation in a photoelectric conversion mode; FIG. 6C shows the operation in a saturated state.

The abscissas of FIGS. 6A to 6C indicate the state in the film thickness direction of each layer shown in FIG. 5. Me1 denotes the lower electrode (G electrode) formed of the first metal thin film layer 104 (e.g. Cr). An amorphous silicon nitride (a-SiNx) insulation thin film layer 111 is an insulating layer for obstructing both of electrons and holes. The layer 111 should have a thickness thicker than one at which a tunnel effect is generated, and consequently the thickness thereof is generally set to be 50 nm or more. An amorphous silicon hydride (a-Si:H) semiconductor thin film layer 112 is a photoelectric conversion semiconductor layer formed of an intrinsic semiconductor layer (i-layer) in which no dopants are intentionally doped. An $N^+$ layer 113 is an obstruction layer of the injection of simple conductivity type carriers, which layer is formed of non-single crystal semiconductor such as N-type a-Si:H layer provided for obstructing the injection of holes into the a-Si:H semiconductor thin film layer 112. Moreover, Me2 indicates the upper electrode (D electrode) formed of the second metal thin film layer 105 (e.g. Al).

Although the D electrodes 105 do not cover the $N^+$ layers 113 completely in FIG. 5, because electron movements are freely performed between the D electrodes 105 and the $N^+$ layers 113, the D electrodes 105 and the N+ layers 113 always have the same electric potential. In the following descriptions, the fact is premised.

Each of the photoelectric conversion elements 101 has two kinds of operation modes of the refresh mode and a photoelectric conversion mode on the methods of the application of voltages onto the D electrodes 105 and the G electrodes.

In FIG. 6A showing the refresh mode, negative electric potential is given to a D electrode 105 to a G electrode. Holes denoted by black circles in the i-layer (a-Si:H) are led to the D electrode by the electric field. At the same time, electrons denoted by white circles are injected into the i-layer (a-Si:H). At this time, a part of the holes and the electrons are recombined with each other in the $N^+$ layer and the i-layer (a-Si:H) to disappear. If this state continues for a sufficiently long time, the holes in the i-layer (a-Si:H) are swept out from the i-layer (a-Si:H).

For changing the state of the photoelectric conversion element 101 to the photoelectric conversion mode shown in FIG. 6B from the aforesaid refresh mode, positive electric potential is given to the D electrode to the G electrode. The application of the positive electric potential instantaneously leads the electrons in the i-layer (a-Si:H) to the D electrode. However, because the $N^+$ layer works as the injection obstruction layer, the holes are not led into the i-layer (a-Si:H). When light enters into the i-layer (a-Si:H) in this state, the entered light is absorbed to generate electron-hole pairs. Those electrons are leaded to the D electrode by the electric field, and those holes move in the i-layer (a-Si:H) to reach the interface between the i-layer (a-Si:H) and the a-SiNx insulation thin film layer.

However, because the holes cannot move into the inside of the a-SiNx insulation thin film layer, the holes stay in the i-layer (a-Si:H). At this time, because the electrons move to the D electrode and the holes move to the a-SiNx insulation thin film interface in the i-layer (a-Si:H), a current for keeping the electric neutrality in the photoelectric conversion element 101 flows from the G electrode. The current is in proportion to the entered light because the current corresponds to the electron-hole pairs generated by the light.

After the state of the photoelectric conversion mode shown in FIG. 6B has been kept for a certain period, when the photoelectric conversion element 101 again returns to the refresh mode shown in FIG. 6A, the holes staying in the i-layer (a-Si:H) are led to the D electrode as described above, and at the same time a current corresponding to the holes flows. The quantity of the holes corresponds to the total quantity of the light entered during the photoelectric conversion period. At this time, a current corresponding to the quantity of the electrons injected into the i-layer (a-Si:H) also flows, but the quantity of the current is almost a constant and then the total current can be obtained by subtracting the current corresponding to the flow of the quantity of the electrons from the current corresponding to the flow of the holes. That is, the photoelectric conversion element 101 outputs the quantity of entered light at real time, and at the same time the element 101 can detect the total quantity of the light entered for a certain period.

However, in the case where the period of the photoelectric conversion mode becomes long owing to some reasons, or in the case where the illuminance of entered light is strong, there is the case where no currents flow even if light enters. The phenomenon is caused by numerous holes staying in the i-layer (a-Si:H) as shown in FIG. 6C, which holes make the electric filed in the i-layer (a-Si:H) small to prevent generated electrons from being led to the D electrode, so that the generated electrons are recombined with the holes in the i-layer (a-Si:H). The state is called as the saturated state of the photoelectric conversion element 101. There is a case where a change of the incidence state of the light flows currents unstably. In such a case, a second change of the mode of the photoelectric conversion element 101 to the refresh mode shown in FIG. 6A sweeps out the holes in the i-layer (a-Si:H), and enables a second current flow in proportion to the light in the next photoelectric conversion mode shown in FIG. 6B.

Moreover, although the all of the holes are ideally swept out in the sweeping of the holes in the i-layer (a-Si:H) in the refresh mode in the above description, only the sweeping of a part of the holes does not causes any problems because the partial sweeping also brings about an effect to make it possible to obtain the same current as that describe above. That is, it is necessary not to be in the saturated state shown in FIG. 6C in a detection chance in the next photoelectric conversion mode, and it is necessary to determine the electric potential of the D electrode to the G electrode in the refresh mode, the period of the refresh mode and the characteristic of the injection obstruction layer of the $N^+$ layer.

Moreover, further injection of electrons into the i-layer (a-Si:H) in the refresh mode is not a necessary condition, and the electric potential of the D electrode to the G electrode is not limited to be negative. The reason is that, when many holes are staying in the i-layer (a-Si:H), the electric field in the i-layer (a-Si:H) is produced to be in the direction of leading the holes to the D electrode even if the electric potential of the D electrode to the G electrode is positive potential. Moreover, it is also not a necessary condition of the characteristic of the $N^+$ layer, which is the injection obstruction layer, to be able to inject electrons into the i-layer (a-Si:H) similarly.

In the embodiment of the radiation imaging apparatus of the present invention, a subtraction process may be performed after a gradation conversion process or an edge enhancement process is performed as the need arises to a (2m−1)th odd image or a 2mth even image in advance at the time of the performance of the subtraction process.

Moreover, a material including $Gd_2O_2S$, $Gd_2O_3$, CsI or the like as the principal component can be used as the material of the X-ray visible conversion phosphor 502. Moreover, the MIS type sensors are exemplified as the photoelectric conversion elements, but positive-intrinsic-negative (PIN) type sensors may be used as the photoelectric conversion elements. Moreover, the photoelectric conversion elements may be formed from lead iodide, mercuric iodide, selenium, cadmium telluride, gallium arsenide, gallium phosphide, zinc sulfide, silicon and the like, and the radiations which have penetrated the subject 507 may be directly converted into electric signals without using the X-ray visible conversion phosphor 502 as the X-ray detector.

According to the present embodiment, X-rays having different energy from each other are alternately irradiated at the time of the producing of the (2m−1)th odd image and at the time of the producing of the 2mth even image while radiographing, and a processed image obtained by performing a subtraction process between the odd image and the even image is displayed on the CRT display 506. Consequently, the display of the parts where the degrees of changes are larger can be enhanced to be blacker or whiter against that of the parts where the degrees of changes are not so larger. Thereby, for example, a doctor can recognize the parts where the degrees of changes are larger while performing the interpretation of a radiograph when the doctor performs a diagnosis. Consequently, the detection rate of abnormal parts such as foci can be improved.

Moreover, in chest simple X-ray radiography, the shadows of bone portions such as costae and clavicles can be removed or decreased while foci lurking in the shadows of (behind) the costae, the clavicles, a diaphragm, a heart and the like, which cannot be obtained only from still images, can be revealed in the movement of the diaphragm and a lung field region owing to the breathing of a patient. Consequently, the detection rate of abnormal parts such as foci can be improved, and a misdiagnosis rate can be decreased. Moreover, the similar effects can be expected to the parts where a plurality of tissues having different absorption characteristics to X-ray energy such as joints composed of bones and tendons (muscles) as well as to the chest portion X-ray radiography.

Such digitalization in medical scenes makes it possible to heighten the efficiency of diagnoses of a doctor in a hospital and the efficiency of works for the management of the hospital. Then, medical environments having higher qualities than those at present can be produced in a future aging society and an information technology (IT) society.

As many apparently widely different embodiments of the present invention can be made without departing from the spirit and scope thereof, it is to be understood that the invention is not limited to the specific embodiments thereof except as defined in the claims.

What is claimed is:

1. A radiation imaging apparatus comprising:
   radiation detection means including radiation detection elements for detecting radiations which have penetrated an object as electric signals, said elements arranged in a two-dimensional array; and
   image display control means for producing a radiation image of the object detected as the electric signals with said radiation detection means as continuous images including a plurality of frames, said image display control means switching a tube voltage of a radiation source for emitting the radiations between a first voltage at a time of producing odd images and a second voltage at a time of producing even images, said image display control means further controlling a display device to continuously display a plurality of processed images as a dynamic image, each of the processed images being obtained by performing a subtraction process between an odd image of the odd images and an even image of the even images, wherein the even image is derived in succession to the odd image.

2. A radiation imaging apparatus according to claim 1, wherein said image display control means performs the subtraction process after performing a gradation conversion process or an edge enhancement process to the odd image or the even image as occasion demands.

3. A radiation imaging apparatus according to claim 1, wherein said radiation detection elements include wavelength conversion bodies for converting the radiations into visible light and photoelectric conversion elements for converting the visible light converted by said wavelength conversion bodies.

4. A radiation imaging apparatus according to claim 3, wherein said wavelength conversion bodies each include a principal component selected from the group consisting of $Gd_2O_2S$, $Gd_2O_3$, CsI.

5. A radiation imaging apparatus according to claim 3, wherein said photoelectric conversion elements are MIS type sensors or PIN type sensors, both using amorphous silicon semiconductor.

6. A radiation imaging apparatus according to claim 5, wherein
   each of said MIS type sensors is configured to include a first metal thin film formed as a lower part electrode, an insulating layer formed on said first metal thin film layer for obstructing electrons and holes, said insulating layer made from amorphous silicon nitride, a photoelectric conversion layer formed on said insulating layer, said photoelectric conversion layer made from amorphous silicon hydride, an N type injection obstruction layer formed on said photoelectric conversion layer for obstructing injections of the holes, and a transparent electrode layer formed on said injection obstruction layer as an upper electrode or a second metal thin film layer formed on said injection obstruction layer, and
   said radiation imaging apparatus supplies an electric field to each of said MIS type sensors in a direction to lead the holes from said photoelectric conversion layer to the second metal thin film layer in a refresh mode, and
   said radiation imaging apparatus supplies an electric field to each of said MIS type sensors in a direction in which the holes generated by the radiations, which have entered said photoelectric conversion layer, are stayed at said photoelectric conversion layer and the electrons are led to said second metal thin film layer in a photoelectric conversion mode, and further
   said radiation imaging apparatus detects the holes accumulated in said photoelectric conversion layer in said photoelectric conversion mode or the electrons led to said second metal thin film layer as light signals.

7. A radiation imaging apparatus according to claim 1, wherein
   said radiation detection elements are made from a material selected from the group consisting of lead iodide, mercuric iodide, selenium, cadmium telluride, gallium arsenide, gallium phosphide, zinc sulfide and silicon, said material absorbs the radiations to convert the absorbed radiations into the electric signals directly.

8. A radiation imaging system comprising:
   a radiation source for emitting radiations; and
   a radiation imaging apparatus including radiation detection means having radiation detection elements for detecting the radiations, which have been emitted from said radiation source and have penetrated an object, as electric signals, said elements arranged in a two-dimensional array; and image display control means for producing a radiation image of the
   object detected as the electrical signals with said radiation detection means as continuous images including a plurality of frames, said image display control means switching a tube voltage of said radiation source for emitting the radiations between a first voltage at a time of producing odd images and a second voltage at a time of producing even images, said image display control means further controlling a display device to continuously display a plurality of processed images as a dynamic image, each of the processed images being obtained by performing a subtraction process between an odd image of the odd images and an even image of the even images, wherein the even image is derived in succession to the odd image.

9. A radiation imaging method comprising the steps of:
   detecting radiations which have penetrated an object as electric signals using radiation detection elements arranged in a two-dimensional array; and
   producing a radiation image of the object detected as the electric signals at the step of detecting radiations as continuous images including a plurality of frames, and switching a tube voltage of radiation source for emitting the radiations between a first voltage at a time of producing odd images and a second voltage at a time of producing even images, and further controlling a display device to continuously display a processed image as a dynamic image, each of the processed images being obtained by performing a subtraction process between an odd image of the odd images and an even image of the even images, wherein the even image is derived in succession to the odd image.

10. A radiation imaging apparatus comprising:

radiation detection means including radiation detection elements for detecting radiations which have penetrated an object as electric signals; and image display control means for producing a radiation image of the object detected as the electric signals with said radiation detection means as continuous images including a plurality of frames, said image display control means switching an energy of radiation between a first energy at a time of producing odd images and a second energy at a time of producing even images, said image display control means further controlling a display device to continuously display a plurality of processed images as a dynamic image, each of the processed images being obtained by performing a subtraction process between an odd image of the odd images and an even image of the even images, wherein the even image is derived in succession to the odd image.

11. A radiation imaging system comprising:

a radiation source for emitting radiations; and a radiation imaging apparatus including radiation detection means having radiation detection elements for detecting the radiations, which have been emitted from said radiation source and have penetrated an object, as electric signals, said elements arranged in a two-dimensional array; and image display control means for producing a radiation image of the object detected as the electric signals with said radiation detection means as continuous images including a plurality of frames, said image display control means switching an energy of radiation between a first energy at a time of producing odd images and a second energy at a time of producing even images, said image display control means further controlling a display device to continuously display a plurality of processed images being obtained by performing a subtraction process between an odd image of the odd images and an even image of the even images, wherein the even image is derived in succession to the odd image.

12. A radiation imaging system according to claim 11, wherein said radiation source comprises a radiation tube for emitting the radiation in pulse; and a radiation power source for applying to the radiation source a tube voltage, which is switched between a first value for producing the odd image and a second value for producing the even image.

* * * * *

UNITED STATES PATENT AND TRADEMARK OFFICE
CERTIFICATE OF CORRECTION

| | | |
|---|---|---|
| PATENT NO. | : 7,127,031 B2 | Page 1 of 1 |
| APPLICATION NO. | : 10/827435 | |
| DATED | : October 24, 2006 | |
| INVENTOR(S) | : Tadao Endo | |

It is certified that error appears in the above-identified patent and that said Letters Patent is hereby corrected as shown below:

[30] FOREIGN APPLICATION PRIORITY DATA:

After "(65) Prior Publication Data" please insert the following:
--            (30) Foreign Application Priority Data
April 22, 2003 (JP) ........................................ 2003-117236--.

COLUMN 3:

Line 6, "but" should be deleted.

COLUMN 4:

Line 46, "as" should be deleted.
Line 49, "as" should be deleted.

COLUMN 6:

Line 61, "as" should be deleted.

COLUMN 11:

Line 67, "causes" should read --cause--.

Signed and Sealed this

Twentieth Day of November, 2007

JON W. DUDAS
*Director of the United States Patent and Trademark Office*